United States Patent
Kopf-Sill et al.

(10) Patent No.: US 6,752,961 B2
(45) Date of Patent: Jun. 22, 2004

(54) MODIFIED SIPHONS FOR IMPROVING METERING PRECISION

(75) Inventors: Anne R. Kopf-Sill, Portola Valley, CA (US); Carol T. Schembri, San Mateo, CA (US)

(73) Assignee: Abaxis, Inc., Union City, CA (US)

( * ) Notice: Subject to any disclaimer, the term of this patent is extended or adjusted under 35 U.S.C. 154(b) by 103 days.

(21) Appl. No.: 09/834,300

(22) Filed: Apr. 12, 2001

(65) Prior Publication Data

US 2003/0207457 A1 Nov. 6, 2003

Related U.S. Application Data

(63) Continuation of application No. 08/562,327, filed on Nov. 22, 1995, now Pat. No. 6,235,531, which is a continuation of application No. 08/254,406, filed on Jun. 6, 1994, now abandoned, which is a continuation-in-part of application No. 08/115,162, filed on Sep. 1, 1993, now Pat. No. 5,591,643.

(51) Int. Cl.[7] .................................................. G01N 9/30
(52) U.S. Cl. ........................ 422/72; 422/100; 422/102; 436/45; 436/180
(58) Field of Search ........................ 422/72, 100, 102; 436/45, 180

(56) References Cited

U.S. PATENT DOCUMENTS

| | | | |
|---|---|---|---|
| 4,244,916 A | 1/1981 | Guigan | 422/72 |
| 4,314,968 A | 2/1982 | Guigan | 422/64 |
| 4,623,519 A | 11/1986 | Comut et al. | 422/72 |
| 4,689,203 A | 8/1987 | Kaartinen et al. | 422/72 |
| 4,743,558 A | 5/1988 | Guigan | 436/45 |
| 4,761,268 A | 8/1988 | Andersen et al. | 422/72 |
| 4,876,203 A | 10/1989 | Guigan | 436/45 |
| 4,894,204 A | 1/1990 | Comut | 422/72 |
| 4,902,479 A | 2/1990 | Brikus | 422/72 |
| 4,963,498 A | 10/1990 | Hillman et al. | 436/69 |
| 4,999,304 A | 3/1991 | Robertson | 436/45 |
| 5,061,381 A | 10/1991 | Burd | 210/789 |
| 5,071,625 A | 12/1991 | Kelln et al. | 422/72 |
| 5,077,013 A | 12/1991 | Guigan | 422/64 |
| 5,104,813 A | 4/1992 | Besemer et al. | 436/179 |
| 5,122,284 A | 6/1992 | Braynin et al. | 210/782 |
| 5,160,702 A | 11/1992 | Kopf-Sill et al. | 422/72 |
| 5,173,193 A | 12/1992 | Schembri | 210/782 |
| 5,173,262 A | 12/1992 | Burtis et al. | 422/72 |
| 5,186,844 A | 2/1993 | Burd et al. | 210/782 |
| 5,256,376 A | 10/1993 | Callan et al. | 422/102 |
| 5,457,053 A | * 10/1995 | Burd et al. | 436/45 |
| 5,693,233 A | * 12/1997 | Schembri | 210/787 |

OTHER PUBLICATIONS

Tech Update, "*Blood Rotor Test Magic*," Popular Mechanics, Feb. 1993.
Schembri, C. Abstract, "*Centrifugation and Capillary Integrated into a Multiple Analyte Whole Blood Analyzer,*" Abaxis, Inc., Feb. 1993.
Marketing Brochure, Abaxis, Inc., Aug. 1993.

* cited by examiner

Primary Examiner—Jan M. Ludlow
(74) Attorney, Agent, or Firm—Gray, Cary, Ware & Freidenrich LLP

(57) ABSTRACT

The present invention provides centrifugal rotors for delivering a premeasured volume of liquid to a chamber in the rotor. In particular the rotors comprise siphons for delivering a premeasured volume of liquid between a first and a second chamber in the rotor. The siphons of the invention are designed such that the inlet of the siphon on the first chamber is radially outward of the siphon outlet on the second chamber. The first chamber is emptied to a level equivalent to the radial position of the siphon outlet.

6 Claims, 6 Drawing Sheets

MODIFIED SIPHONS FOR IMPROVING METERING PRECISION

The present application is a continuation of U.S. patent application Ser. No. 08/562,327 filed Nov. 22, 1995 now U.S. Pat. No. 6,235,531, which is a continuation of U.S. patent application Ser. No. 08/254,406, filed Jun. 6, 1994, now abandoned which is a continuation in part of U.S. patent application Ser. No. 08/115,162 filed Sep. 1, 1993 now U.S. Pat. No. 5,591,643 each of which is incorporated herein by reference.

BACKGROUND OF THE INVENTION

The present invention relates generally to devices and methods for analyzing biological fluids. In particular, it relates to the design and use of improved centrifugal rotors having siphons which allow delivery of a precise volume of liquid to a chamber in the rotor.

Biological tests of blood plasma and other biological fluids frequently require that fluids be quickly divided into predetermined volumes for analysis in a variety of optical tests or assays. It is also frequently desirable to separate potentially interfering cellular components of the material from the other fluid prior to testing. Such measurement and separation steps have previously been typically performed by centrifugation to separate, for instance, blood plasma from the cellular components, followed by manual or automated pipetting of predetermined volumes of the blood plasma into separate test walls. Such procedures are labor intensive and time-consuming. As a result, various automated systems and methods have been proposed for providing multiple aliquots of plasma suitable for testing in a more efficient manner.

A major advance in the analysis of biological fluids has been the use of centrifugal rotors. These rotors are designed to measure volumes of a biological fluid, such as blood, remove cellular components, and mix the fluid with an appropriate diluents for analysis, for example by optical testing. Typically, the rotors provide a plurality of discrete volumes of sample in separate cuvettes in which the sample is optically analyzed.

To ensure accurate and consistent results, such rotors require the delivery of precisely measured volumes of liquid to various chambers in the rotor. This must often be accomplished in circumstances in which the rotor quickly accelerates and decelerates or is otherwise perturbed during operation. This perturbation can often lead to delivery of inaccurately measured volumes. The present invention addresses these and other needs.

DESCRIPTION OF THE BACKGROUND ART

U.S. Pat. Nos. 4,894,204 and 5,160,702 disclose siphons for transferring fluids between chambers in a rotor. U.S. Pat. No. 4,244,916 discloses a rotor comprising a plurality of cuvettes positioned radially outward of a central receptacle. Each cuvette is connected to the central receptacle by a duct and comprises a separate air escape orifice. U.S. Pat. No. 4,314,968 relates to rotors having cells positioned on the periphery of the rotor. Each cell includes a peripheral orifice for removing fluid introduced into the cell. U.S. Pat. No. 4,902,479 discloses a multicuvette rotor comprising elongated, radially extending cuvettes. Each elongated cuvette comprises a first chamber for receiving a first constituent and a second chamber for receiving a second constituent. A divider structure between the first and second chambers prevents mixing of the constituents before a predetermined time. Mixing occurs as the rotor is spun at a significant speed. U.S. Pat. No. 4,963,498 discloses devices which rely upon capillaries, chambers, and orifices to pump and mix fluids for optical analysis. U.S. Pat. No. 5,077,013 discloses rotors comprising peripheral cuvettes connected to holding chambers positioned radially inward from the cuvettes.

SUMMARY OF THE INVENTION

The present invention provides centrifugal rotors comprising siphons for delivering a premeasured volume of liquid, typically a biological sample such as plasma, between a first and a second chamber in the rotor. The siphons of the invention have an elbow that is radially inward of the radially most inward point of the fluid in the first chamber. As the rotor is spinning the fluid does not flow past the elbow. After the rotor stops, capillary forces "prime" the siphon by pulling fluid just around the elbow. When the rotor is restarted, centrifugal force draws the remaining fluid out of the metering chamber into the receiving chamber until the level of the fluid in the metering chamber is at the same radial distance as the outlet of the siphon. The siphons of the invention are designed such that the inlet of the siphon on the first chamber is radially outward or inward of the siphon outlet on the second chamber.

The positioning of the inlets and outlets of the siphons of the invention provide a number of advantages. For example, the inlet of the siphon is always positioned radially outward of the final position of the meniscus of the fluid in the first chamber, after fluid has been transferred to the second chamber. Thus, inaccuracy in measurement associated with different shaped menisci in different fluids is minimized since the meniscus is minimized.

The chambers connected by the siphons of the invention are used to perform any of a number of functions, such as metering liquids, separating solid components from a sample, mixing diluent with the sample, and the like. In the preferred embodiments, the siphons connect a plasma metering chamber to a mixing chamber for mixing the premeasured volume of plasma with diluent.

In addition, the rotors of the invention comprise unmodified inlet channels connecting a distribution ring to cuvettes comprising reagents for optical analysis of a biological sample. The inlet channels are sized such that, as the rotor spins, gas escapes from the cuvette through the inlet channel as the liquid enters the cuvette through the inlet channel. An "unmodified inlet channel" as used herein refers to a simple inlet channel, typically having a rectangular cross section, which is not modified (e.g., by altering the cross-sectional shape, surface texture, and the like) to provide a pathway for gas to escape from a cuvette that is not otherwise vented.

DESCRIPTION OF THE PREFERRED EMBODIMENT

Figure 1A:
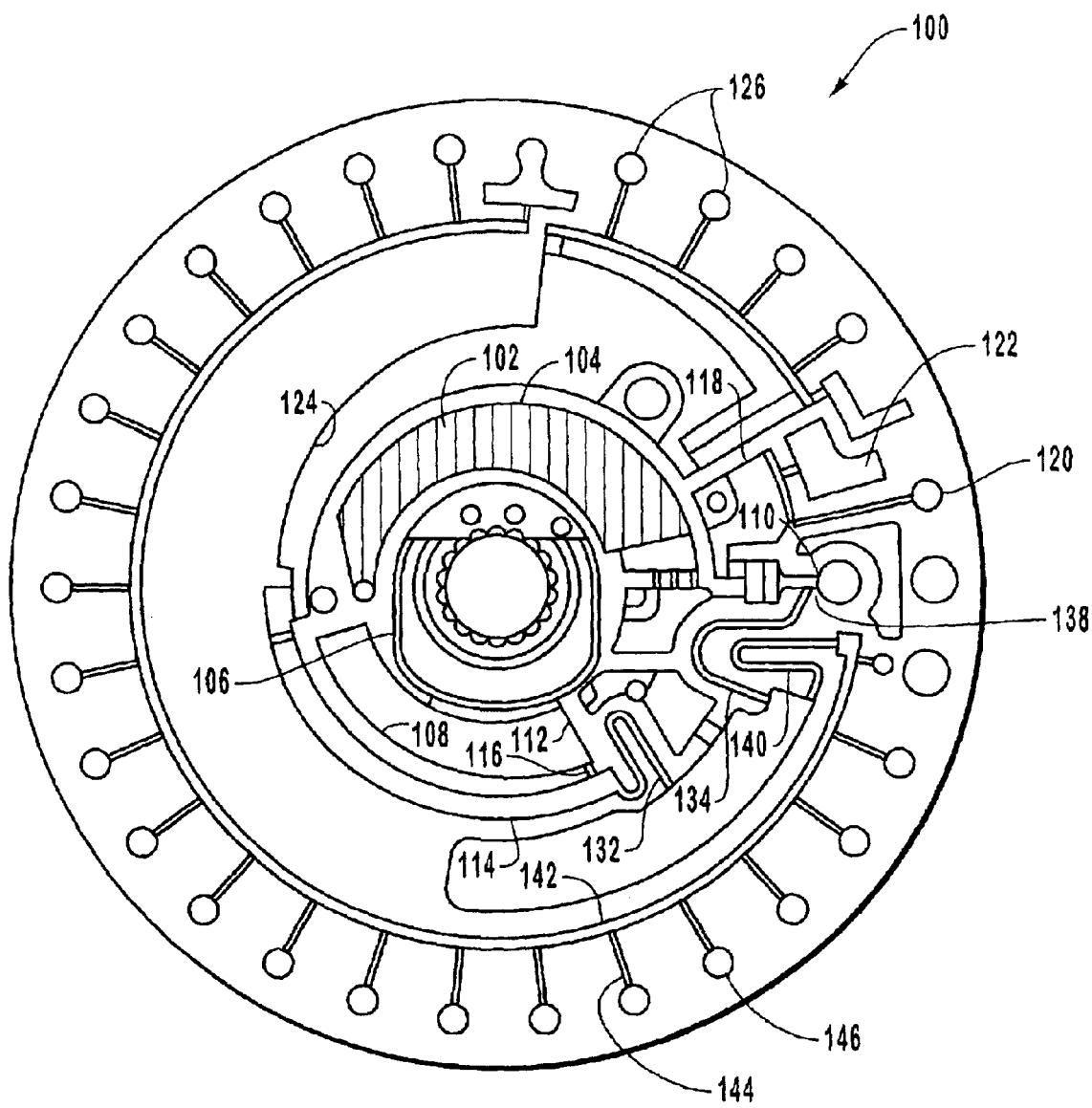
FIGS. 1A–1F are top plan views of a rotor of the invention showing the flow of fluids through the chambers and channels of the rotor as the rotor is spun.

The present invention provides methods and devices for the delivery of liquids to chambers in an analytical rotor. The rotors of the invention comprise siphons which ensure precise delivery of metered volumes of liquid to a desired chamber in the rotor.

The rotors of the invention are suitable for the analysis of any liquid, typically a biological sample such as whole blood or plasma. It is also useful with numerous other biological fluids, such as urine, sputum, semen, saliva, ocular lens fluid, cerebral fluid, spinal fluid, amniotic fluid. Other fluids that can be tested include tissue culture media, food and industrial chemicals, environmental samples and the like.

The rotors typically provide chambers which can separate cellular components from the biological sample (e.g. whole blood), measure a precise volume of liquid sample (e.g. plasma), mix the sample with an appropriate diluent and deliver the diluted sample to cuvettes for optical analysis. The fluid delivered to the cuvettes, undergoes reaction(s) within the cuvettes, e.g., reaction with a reagent which forms part of an analytical procedure to detect one or more analytes within the fluid. The sample may further be optically analyzed while present in the rotor, either with or without prior reaction.

The apparatus of the present invention comprises an analytical rotor having a rotor body which is capable of being mounted on a conventional laboratory centrifuge of the type which is commercially available from suppliers, such as Beckman Instruments, Inc., Spinco Division, Fullerton, Calif.; Fisher scientific, Pittsburgh, Pa.; VWR Scientific, San Francisco, Calif., and the like. Generally, the centrifugal rotor will include a receptacle or other coupling device suitable for mounting on a vertical drive shaft provided by the centrifuge. The particular design of the receptacle or coupling device will depend on the nature of the centrifuge, and it will be appreciated that the centrifugal rotor of the present invention may be adapted for use with all or most types of centrifuges which are now available or which may become available in the future.

The rotor body comprises a structure which maintains a desired geometric pattern or relationship between a plurality of chambers, interconnection passages, and vents, as described in more detail below. Various specialized chambers and channels suitable for use in the rotors of the invention are disclosed in U.S. Pat. Nos. 5,061,381 and 5,122,284, and U.S. Ser. Nos. 07/678,762 and 07/783,041 which are incorporated herein by reference.

Usually, the body will be a substantially solid plate or disk with the chambers and passages formed as spaces or voids in the otherwise solid matrix. Conveniently, such solid plate structures may be formed by laminating a plurality of separately-formed layers together into a composite structure where the chambers and horizontal passages are generally formed between adjacent layers. The vertical passages may be formed through the layers. The individual layers may be formed by injection molding, machining, or combinations thereof, and will usually be joined together, typically using a suitable adhesive or by ultrasonic welding. The final enclosed volumes are formed when the layers are brought together.

Of course, the centrifugal rotor could also be formed as a plurality of discrete components, such as tubes, vessels, chambers, etc., arranged in a suitable framework. Such assemblies of discrete components, however, are generally more difficult to manufacture and are therefore less desirable than those formed within a substantially solid plate.

The rotor body may be formed from a wide variety of materials and may optionally include two or more materials. Usually, the material(s) will be transparent so that the presence and distribution of the biological fluid, cellular components, and reagents may be observed within the various internal chambers and passages. Optionally, to the extent analytical chambers, e.g., cuvettes, or other test wells are formed within the rotor, it is desirable to have suitable optical paths formed within the rotor so that the contents of the cuvettes may be observed spectrophotometrically, fluorometrically, or by other optical assessment instruments. The construction of suitable cuvettes having particular optical paths formed therethrough is disclosed in U.S. Pat. No. 5,173,193, the disclosure of which is incorporated herein by reference. In the preferred embodiment, the rotor is formed with an acrylic resin having suitable optical properties, at least in those areas which define an optical path.

The apparatus and method of the present invention are suitable for performing a wide variety of analytic procedures and assays which are beneficially or necessarily performed on blood plasma and other samples. The analytic procedures may require that the sample be combined with one or more reagents so that some detectable change occurs which may be related to the presence and/or amount of a particular component (analyte) or characteristic of the sample. For instance, the sample may undergo a reaction or other change which results in a change in color, fluorescence, luminescence, or the like, which may be measured by conventional spectrophotometers, fluorometers, light detectors, and the like. In some cases, immunoassays and other specific binding assays may be performed within the cell-free fluid collection chamber or within cuvettes which are connected to the collection chamber. Generally, such assay procedures should be homogeneous and not require a separation step. In other cases, however, it may be possible to accommodate heterogeneous assay systems by providing a means to separate the sample (e.g., blood plasma) from the collection chamber or another test well or cuvette after the immunological reaction step has occurred. One of skill will recognize that the means of analyzing the sample is not an important aspect of the invention. Any of a number of analytical methods can be adapted for use in the rotors of the invention, depending upon the particular sample being analyzed and component being detected.

In the case of blood analyses, conventional blood assays are typically performed. Examples of assays which may be performed include those designed to detect glucose, lactate, dehydrogenase, serum glutamic-oxaloacetic transaminase (SGOT), serum glutamic-pyruvic transaminase (SGPT), blood urea nitrogen (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood and plasma be combined with one or more reagents which result in an optically detectable, usually photometrically detectable, change in the plasma. The reagents which are required are well known and amply described in the patent and scientific literature.

The reagents are preferably provided in lyophilized form to increase stability. Ideally, they are provided in the form of lyophilized reagent spheres as described in U.S. Ser. No. 07/747,179, which is incorporated herein by reference.

Referring now to FIGS. 1A–1F, an analytical rotor comprising the chambers and channels of the present invention can be seen. FIG. 1A shows the position of a blood sample 102 in the blood application chamber 104 after the sample has been loaded in the rotor body 100. A diluent container in chamber 106 is opened upon mounting of the rotor on the spindle of the centrifuge as described in copending and commonly assigned application, U.S. Ser. No. 07/873,327, which is incorporated herein by reference.

Figure 1B:
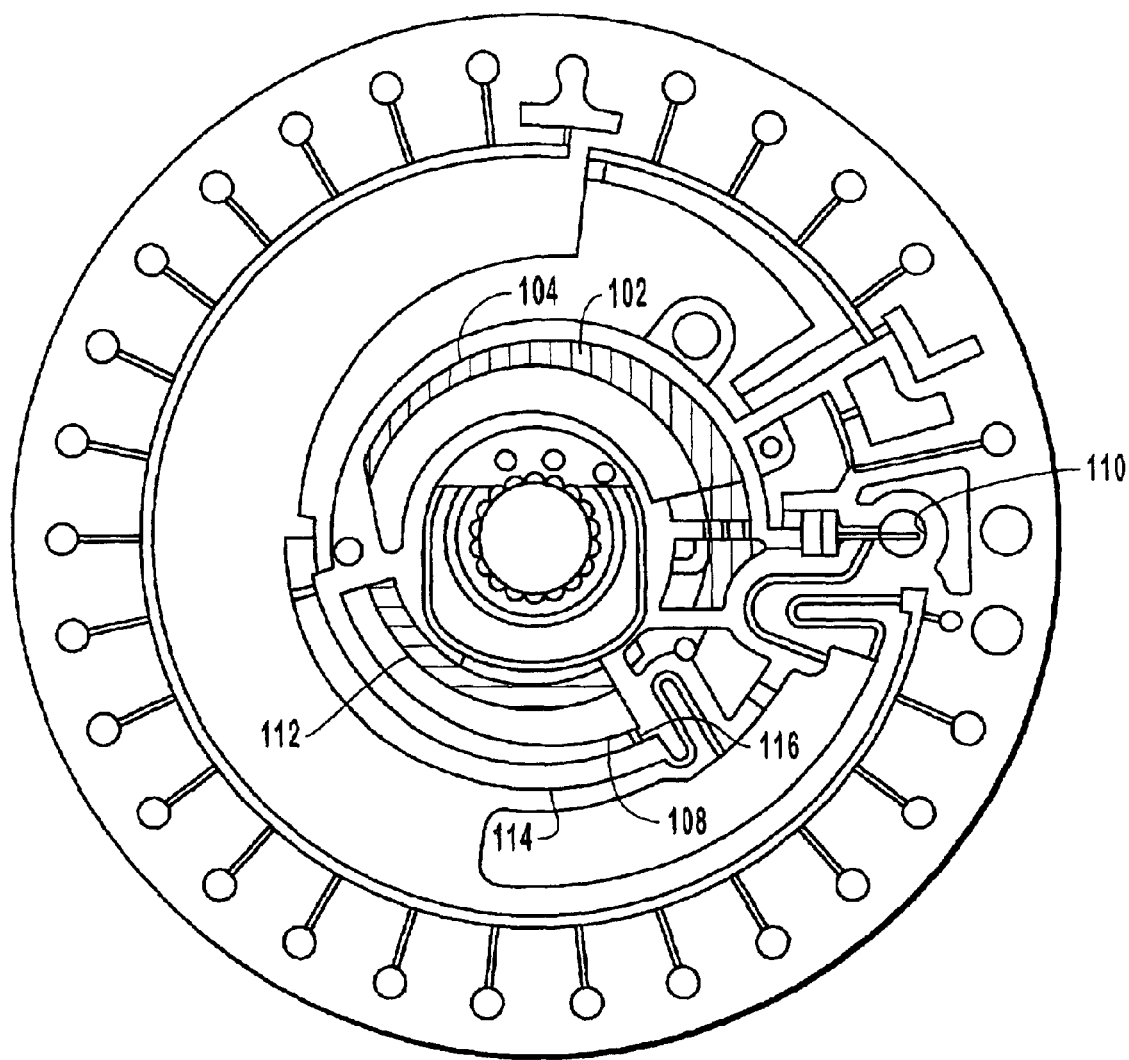

FIG. 1B shows the position of the diluent 108 and blood sample 102 after the rotor is spun at 4,000 rpm. The blood sample 102 begins to exit the blood application chamber 104 and enters the plasma metering chamber 110. At the same time, diluent 108 empties from the diluent container into the holding chamber 112. The diluent immediately begins to enter the diluent metering chamber 114 through channel 116.

Figure 1C:
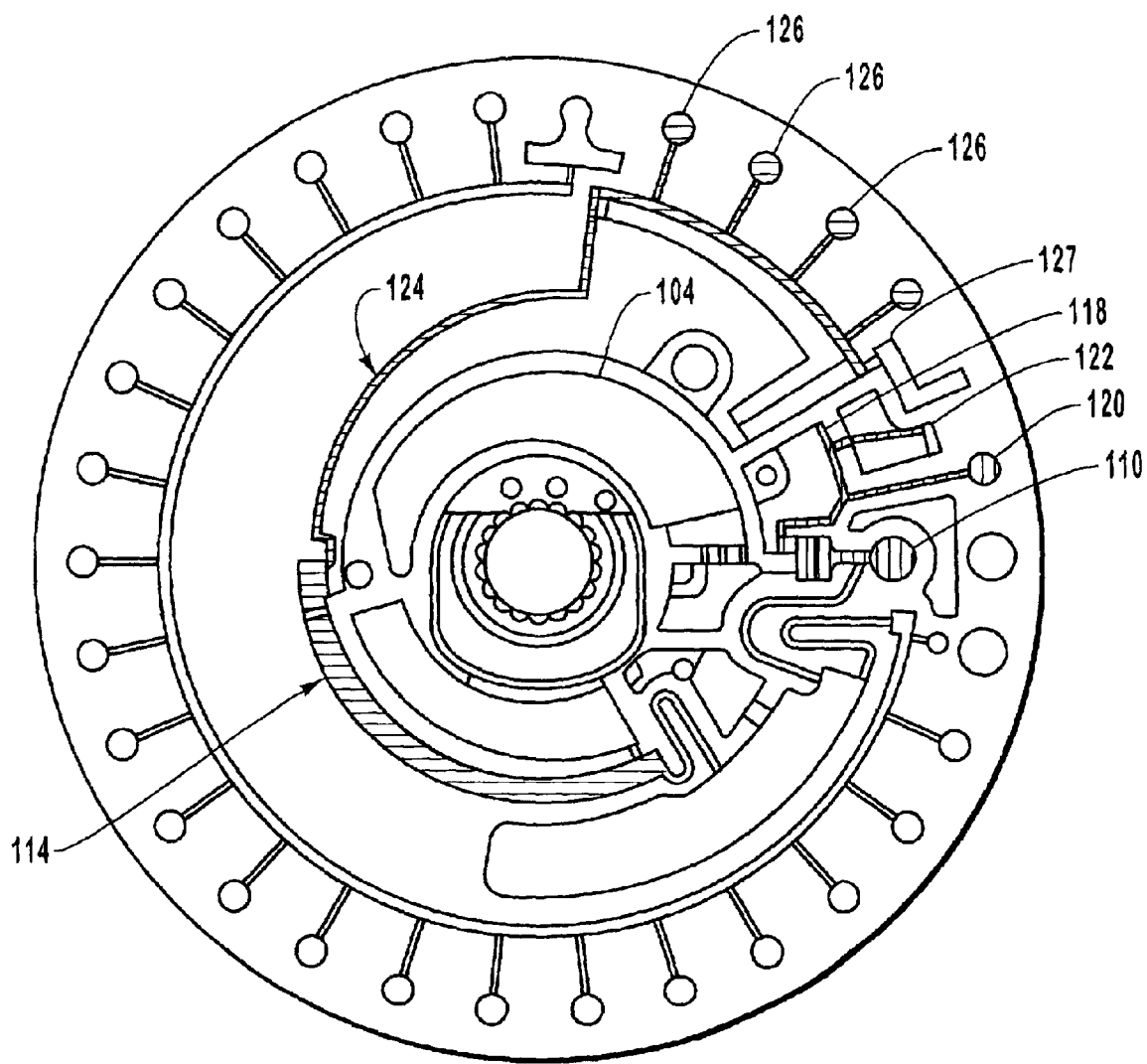

FIG. 1C shows the position of the liquids as the rotor 100 continues to spin. Here, the blood sample 102 has emptied the blood application chamber 104 and overflows the plasma metering chamber 110 into the overflow chamber 118 where it flows to the hemoglobin cuvette 120 and the excess blood dump 122. Meanwhile, diluent 108 fills the diluent metering chamber 114 and excess flows through channel 124 to diluent-only cuvettes 126 and excess diluent dump 127.

Figure 1D:
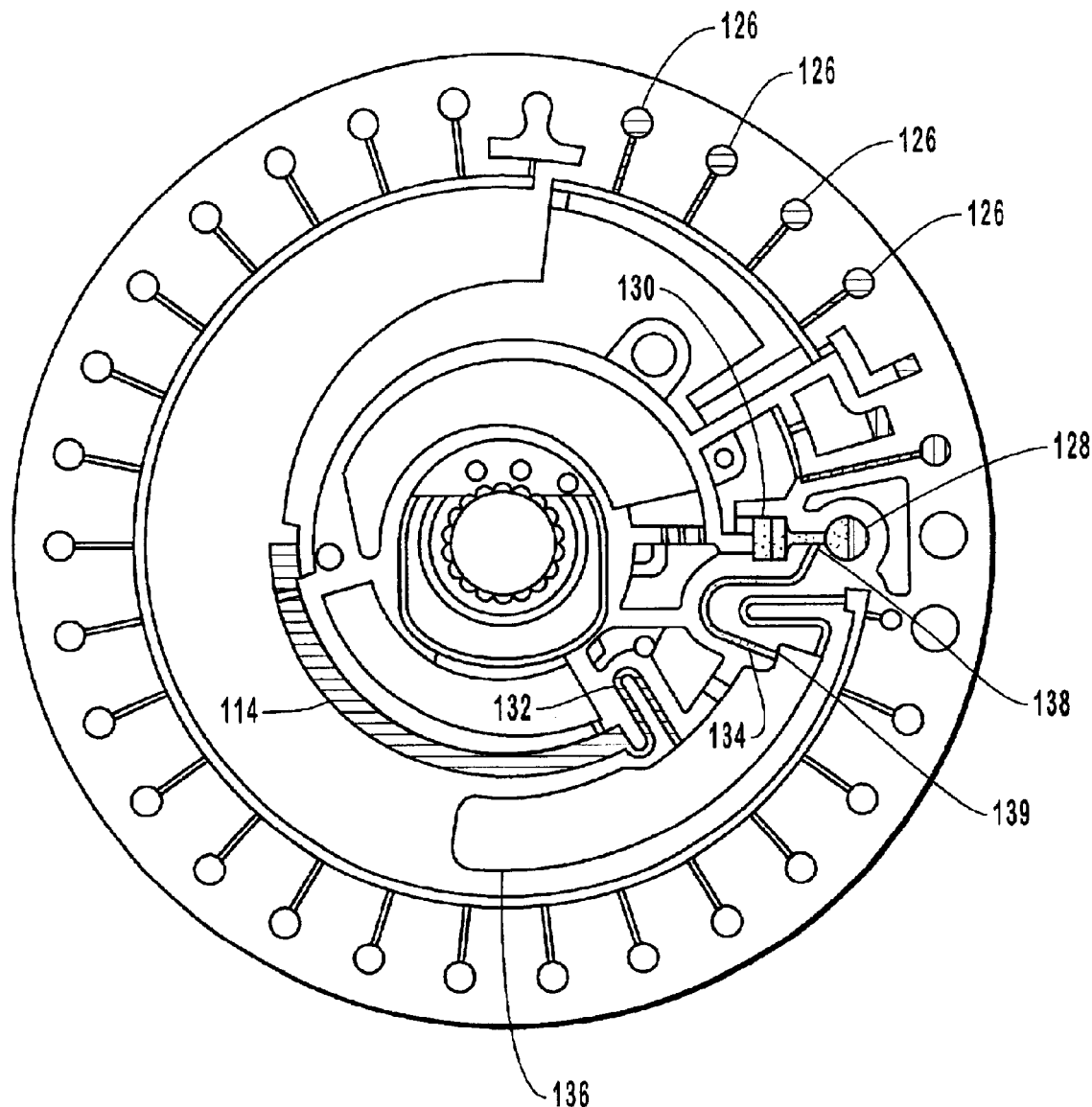

FIG. 1D shows the position of the liquids at the conclusion of the first spin. The blood sample 102 has separated into cells 128 and plasma 130. The diluent-only cuvettes 126 are filled and a predetermined amount of diluent remains in the diluent metering chamber 114. The rotor 100 is then stopped and the siphon 132 from the diluent metering chamber 114, as well as the siphon 134 from the plasma metering chamber 110, are allowed to prime, as described above. Siphon 134 is a siphon of the present invention. It is connected to the plasma metering chamber 110 at inlet 138. The inlet 138 is positioned radially outward of the siphon outlet 139, through which the siphon 134 empties into the mixing chamber 136.

Figure 1E:
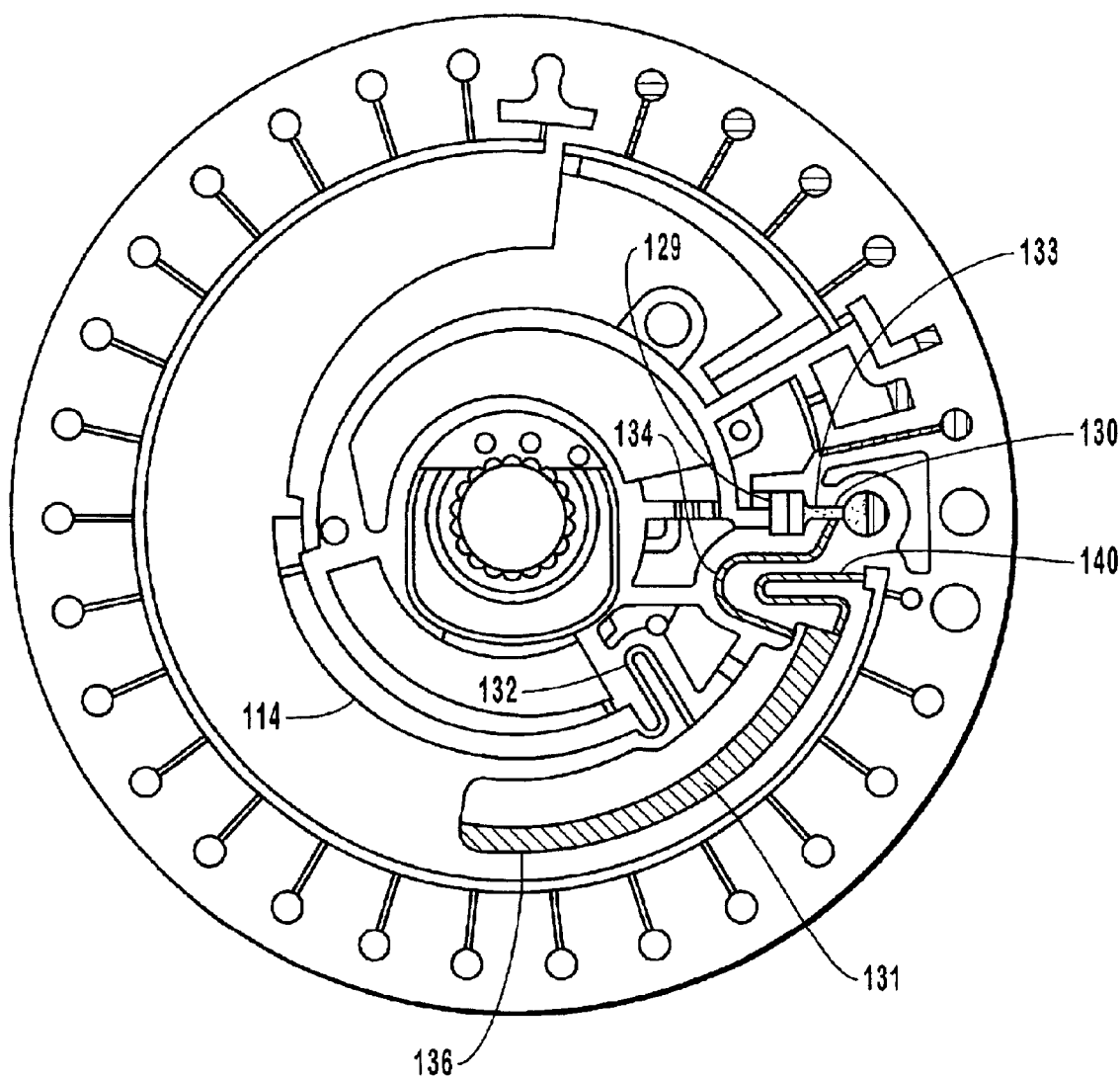

FIG. 1E shows the position of the liquids during the second spin of the rotor. The diluent metering chamber 114 empties into the mixing chamber 136 through siphon 132. A predetermined amount of plasma 130 is metered into the mixing chamber 136 and the two fluids are mixed, thereby forming diluted plasma 131. The amount of plasma 130 delivered to the mixing chamber 136 is determined by the position of the outlet 139 on the siphon 134. As can be seen in this figure, the final level of the plasma 133 in the plasma metering chamber 110 is at the same radial position as the outlet 139. Thus, the volume of plasma delivered to the mixing chamber 136 is determined by the volume of the plasma metering chamber 110 between the exit to the overflow chamber 129 and the final level of plasma 133. After the plasma and diluent are mixed in the mixing chamber 136, the rotor is stopped again and the output siphon 140 is primed.

Figure 1F:
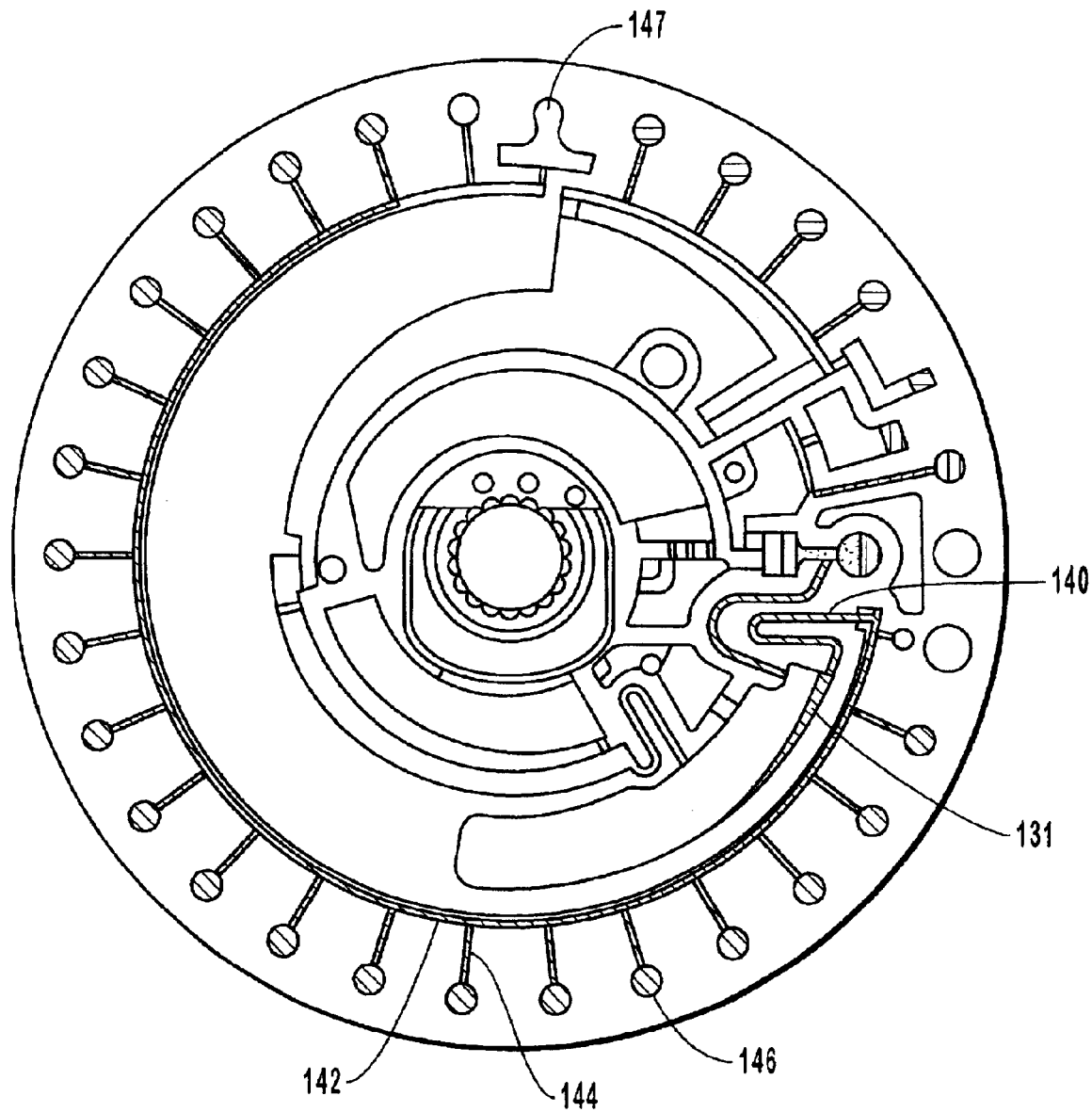

FIG. 1F shows the position of the diluted plasma 131 as the rotor is spun during the third spin. This figure illustrates the movement of the diluted plasma 131 through the distribution ring 142 and inlet channels 144 to the cuvettes 146 and excess plasma dump 147. The resistance to flow in the output siphon 140 is selected to be higher than the resistance to flow in the distribution ring 142 and the inlet channels 144 50 that air present in the cuvettes 146 can escape as the cuvettes are filled. Specifically, siphon 140 is dimensioned such that the ratio of the cross sectional area of the inlet channels 144 to the cross sectional area of the liquid in them is greater than 2:1, preferably greater than about 4:1. The cross sectional area of the inlet channels 144 is typically the same as or slightly smaller than that of the distribution channel 142 so that gas in the unvented cuvettes escapes through the inlet channels 144 and distribution 142. The cross-sectional area of the inlet channel 144 usually is larger than the cross sectional area of the delivery channel 140, e.g., at least about 1.5 times or 2 times the cross-sectional area of the delivery channel 140. If the sample is plasma or diluted plasma and the channels are rectangular in cross-section, their dimensions are typically as follows: siphon: 0.150 mm depth, 0.200 mm width; distribution channel 0.300 mm depth, 0.5 mm width; inlet channels: 0.150 depth, 0.500 width.

After the cuvettes have been filled, reagents present in the cuvettes are mixed with the solution and the necessary photometric analyses are made on the sample. Such analyses are carried out as described above according to methods known to those of skill in the art.

Although the foregoing invention has been described in detail for purposes of clarity of understanding, it will be obvious that certain modifications may be practiced within the scope of the appended claims.

What is claimed is:

1. A centrifugal rotor comprising:

a rotor body comprising a liquid-dispensing chamber, a liquid-receiving chamber, and a siphon;

the siphon being connected to the liquid-dispensing chamber through a siphon inlet and connected to the liquid-receiving chamber through a siphon outlet, the siphon inlet being radially inward of the siphon outlet, said siphon traveling radially outward to a point radially outward of said liquid-dispensing chamber then radially inward to a point radially inward of said siphon inlet and then radially outward to said siphon outlet; the rotor further comprising:

a cuvette containing reagents necessary for the analysis of a biological sample, wherein said cuvette is radially outward of said liquid-dispensing chamber and said liquid-receiving chamber, and;

a distribution ring which permits flow of a liquid to said cuvette from an output siphon connected to the liquid-receiving chamber.

2. A centrifugal rotor comprising:

a rotor body comprising a liquid-dispensing chamber, a liquid-receiving chamber, and a siphon;

the siphon being connected to the liquid-dispensing chamber through a siphon inlet and connected to the liquid-receiving chamber through a siphon outlet, the siphon inlet being radially inward of the siphon outlet, said siphon traveling radially outward to a point radially outward of said liquid-dispensing chamber then radially inward to a point radially inward of said siphon inlet and then radially outward to said siphon outlet; the rotor further comprising:

a distribution ring positioned radially outward of the liquid receiving chamber; and a delivery channel connecting the distribution ring to the liquid-receiving chamber, said distribution ring being connected to a cuvette through an inlet channel.

3. The rotor of claim 2, wherein the inlet channel has a cross sectional area at least about 1.5 times the cross sectional area of the delivery channel.

4. The rotor of claim 3, wherein the cross sectional area of the inlet channel is about 2 times the cross sectional area of the delivery channel.

5. The rotor of claim 3, wherein the cross sectional area of the delivery channel is about 0.03mm$^2$.

6. The rotor of claim 2, wherein the delivery channel is a siphon.

* * * * *